Sept. 24, 1974 F. W. ANDERSON Plant Pat. 3,626
APRICOT TREE
Filed Aug. 23, 1973
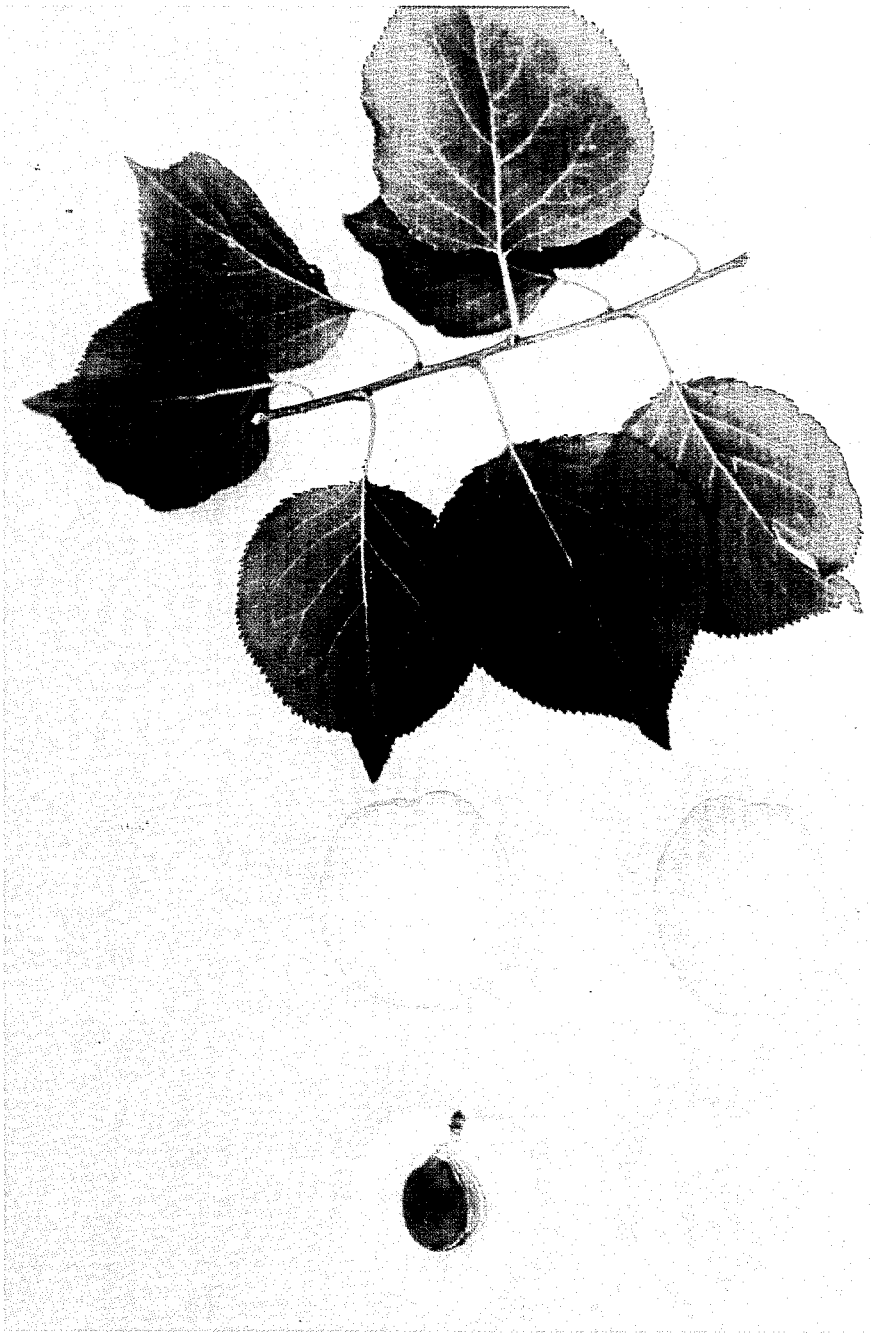

United States Patent Office

Plant Pat. 3,626
Patented Sept. 24, 1974

3,626
APRICOT TREE

Frederic W. Anderson, Merced, Calif., assignor to The Burchell Nursery, Inc., Modesto, Calif.

Filed Aug. 23, 1973, Ser. No. 391,011
Int. Cl. A01h 5/03
U.S. Cl. Plt.—39 1 Claim

ABSTRACT OF THE DISCLOSURE

An apricot tree which is large, vigorous, spreading, foliated with large, cordate leaves having a crenate margin, and a regular and very productive bearer of uniform, large, globose-to-oblong, freestone fruit having yellow skin and yellow flesh.

Background of the variety: Over a substantial number of years I have engaged in an extensive and continuing plant breeding program at my experimental nursery and orchard located near Le Grand, Merced County, Calif.; one purpose of such program being to provide improved varieties of fruit trees. The present variety of apricot tree resulted from my endeavors in the conduct of such plant breeding program.

Origin of the variety: The present variety of apricot tree was originated by me, in my aforesaid experimental nursery and orchard, as a $F_2$ seedling of a cross between the Perfection and the Tilton (both unpatented) apricots.

Asexual reproduction of the variety: Upon recognition by me of the novel and distinct characteristics of the present variety of apricot tree, I asexually reproduced it by budding on seedling apricot trees planted in my said experimental orchard. In maturity, such reproductions ran true, in all respects, to the original tree of the variety.

Summary of the variety: The present variety of apricot tree is large, vigorous, spreading, foliated with large, cordate leaves having a crenate margin, and a regular and very productive bearer of uniform, large, globose-to-oblong, freestone fruit having yellow skin and yellow flesh; the variety—in comparison to the Tilton, and which is presently the leading variety of apricot in California—both blooming and bearing fruit which ripens about three to four days later, and is larger, firmer, borne regularly and more productively, less susceptible to flesh discoloration next to the pit cavity at harvest time, and of better eating quality whether fresh, frozen, dried, or canned.

Brief description of the drawing: The drawing is an illustration, by photographic reproduction in color, of a twig with leaves, and separate fruit; one of the latter being cut into halves, with the stone remaining in one half.

Description of the variety: The botanical details of this new and distinct variety of apricot tree—with color definitions referenced to Maerz and Paul Dictionary of Color (except where common terms of color definitions are employed)—are as follows:

Tree
- *Size.*—Large.
- *Vigor.*—Vigorous.
- *Growth.*—Spreading.
- *Production.*—Very productive.
- *Bearing.*—Regular bearer. Bears well even with unfavorable weather at blooming time.

Trunk
- *Size.*—Stocky.

Branches
- *Size.*—Medium.
- *Texture.*—Smooth.

Leaves
- *Size.*—Large. Average length—3¼". Average width —3".
- *Form.*—Cordate. Abruptly pointed.

- *Thickness.*—Medium.
- *Texture.*—Smooth.
- *Margin.*—Crenate.
- *Petiole.*—Medium length. Medium thickness.
- *Glands.*—Average number—3 to 4 on petiole, and 2 on blade. Alternate. Small. Globose.
- *Color.*—Topside—Medium green (23–L–7). Under side—Lighter green (22–H–7).

Flower buds
- *Size.*—Large.
- *Length.*—Medium.

Flowers
- *Blooming Period.*—Usually 3 or 4 days after Tilton. Late, as compared with other varieties.
- *Size.*—Medium.
- *Color.*—White.

Fruit
- *Maturity When Described.*—Hard ripe—July 14th, 1973.
- *Date of First Picking.*—July 10th, 1973.
- *Date of Last Picking.*—July 20th, 1973.
- *Size.*—Uniform. Large. Average diameter axially—2". Average transversely in suture plane—1⅞".
- *Form.*—Uniform. Symmetrical. Globose to oblong. Compressed laterally.
- *Suture.*—Shallow.
- *Ventral Surface.*—Rounded.
- *Cavity.* — Round. Average depth — ¼". Average breadth—¼".
- *Base.*—Rounded.
- *Apex.*—Very short.

Skin
- *Thickness.*—Medium.
- *Texture.*—Medium.
- *Tendency To Crack.*—Slight.
- *Down.*—Scant. Short.
- *Color.*—Apricot yellow (10–J–6) shading deeper to (10–L–8).

Flesh
- *Texture.*—Firm. Crisp. Meaty.
- *Fibers.*—Few.
- *Ripens.*—Evenly.
- *Flavors.*—Subacid. Mild.
- *Acidity.*—Low—averages pH.4.15 to 4.40.
- *Eating Quality.*—Good.
- *Color.*—Apricot yellow (10–L–93). Surface of pit cavity—Yellow.

Stone
- *Type.*—Free. Parts from flesh smoothly.
- *Size.* — Medium. Average length — 1¼". Average breadth—⅞". Average thickness—½".
- *Form.*—Oblong.
- *Base.*—Straight.
- *Apex.*—Rounded.
- *Sides.*—Equal. Flattened.
- *Ventral Edge.*—Thick.
- *Dorsal Edge.*—Narrow, with shallow groove toward base.
- *Tendency To Split.*—None noted.
- *Color.*—Brown (8–H–9).

Use
- *Market.*—Local. Dessert. Canning. Freezing.

Keeping quality: Good.

Resistance to insects and diseases: No unusual susceptibilities noted.

The apricot tree and its fruit herein described may vary in slight detail due to climatic and soil conditions under which the variety may be grown; the present description being of the variety as grown in the Central Valley of California.

I claim:

1. A new and distinct variety of apricot tree, substantially as illustrated and described, which is large, vigorous, spreading, foliated with large, cordate leaves having a crenate margin, and a regular and very productive bearer of uniform, large, globose-to-oblong, freestone fruit having yellow skin and yellow flesh; the variety—in comparison to the Tilton—both blooming and bearing fruit which ripens about three to four days later, and is larger, firmer, borne regularly and more productively, less susceptible to flesh discoloration next to the pit cavity at harvest time, and of better eating quality.

No references cited.

ROBERT E. BAGWILL, Primary Examiner